United States Patent
Hamed et al.

(10) Patent No.: US 7,686,921 B2
(45) Date of Patent: Mar. 30, 2010

(54) LIQUID DISTRIBUTION MAT MADE OF ENHANCED CELLULOSIC FIBERS

(75) Inventors: Othman A. Hamed, Jesup, GA (US); Harry J. Chmielewski, Brunswick, GA (US)

(73) Assignee: Rayonier TRS Holding Inc., Jessup, GA (US)

( * ) Notice: Subject to any disclaimer, the term of this patent is extended or adjusted under 35 U.S.C. 154(b) by 663 days.

(21) Appl. No.: 11/414,218

(22) Filed: May 1, 2006

(65) Prior Publication Data

US 2007/0254550 A1 Nov. 1, 2007

(51) Int. Cl.
*D21H 11/20* (2006.01)
*D21H 21/20* (2006.01)
*D21H 21/22* (2006.01)
*D21H 23/24* (2006.01)

(52) U.S. Cl. ................. 162/157.6; 162/146; 162/164.1; 162/184; 604/375

(58) Field of Classification Search ................. 162/146, 162/157.1, 157.6, 158, 164.1, 168.1, 182–186, 162/72, 75, 76; 604/370, 374–376
See application file for complete search history.

(56) References Cited

U.S. PATENT DOCUMENTS

| | | | |
|---|---|---|---|
| 3,224,926 A | 12/1965 | Bernardin | |
| 3,241,533 A | 3/1966 | Balmer | |
| 3,575,174 A | 4/1971 | Mogor | |
| 3,756,913 A | 9/1973 | Wodka | |
| 4,035,147 A | 7/1977 | Sangenis et al. | |
| 4,699,619 A | 10/1987 | Bernardin | |
| 4,781,710 A | 11/1988 | Megison et al. | |
| 4,822,453 A * | 4/1989 | Dean et al. ................ 162/157.6 |
| 5,124,197 A * | 6/1992 | Bernardin et al. ............. 442/35 |
| 5,183,707 A | 2/1993 | Herron et al. | |
| 5,190,563 A | 3/1993 | Herron et al. | |
| 5,225,047 A | 7/1993 | Graef et al. | |
| 5,244,482 A | 9/1993 | Hassenboehler et al. | |
| 5,268,224 A | 12/1993 | DesMarais et al. | |
| 5,281,207 A | 1/1994 | Chmielewski et al. | |
| 5,350,370 A | 9/1994 | Jackson et al. | |
| 5,427,587 A | 6/1995 | Arkens et al. | |
| H1511 H | 12/1995 | Chappell et al. | |
| 5,549,589 A | 8/1996 | Horney et al. | |

(Continued)

OTHER PUBLICATIONS

Electronic Mail Message from Elson Silva, Ph.D., dated May 3, 2006 with alleged explanation of relevance. [Note: Applicants and their counsel did not prepare, modify or otherwise alter this explanation, which was apparently prepared by Dr. Silva, and therefore expressly disclaim any representation(s) regarding the accuracy of that explanation.]

*Primary Examiner*—Eric Hug
(74) *Attorney, Agent, or Firm*—Hunton & Williams LLP (57) ABSTRACT

A liquid distribution mat that is a wet-laid mat of enhanced cellulosic fibers that are cellulosic fibers cross-linked in sheet form, as well as methods of making the liquid distribution mat. The liquid distribution mat has high vertical wicking properties and excellent structural integrity in both wet and dry states. The liquid distribution mat is suitable for use in an absorbent article. When used in an absorbent article such as a baby diaper, the liquid distribution mat rapidly acquires and transports bodily discharges from the point of insult to other regions of the absorbent article, thereby maximizing the utilization of the absorbent article.

32 Claims, 4 Drawing Sheets

U.S. PATENT DOCUMENTS

| | | | |
|---|---|---|---|
| 5,549,791 A * | 8/1996 | Herron et al. | 162/157.6 |
| 5,755,828 A | 5/1998 | Westland | |
| 5,800,416 A * | 9/1998 | Seger et al. | 604/366 |
| 5,965,466 A | 10/1999 | Rodrigues et al. | |
| 5,998,511 A * | 12/1999 | Westland et al. | 524/13 |
| 6,068,620 A | 5/2000 | Chmielewski | |
| 6,290,867 B1 | 9/2001 | Kielbania et al. | |
| 6,620,293 B2 * | 9/2003 | Sears et al. | 162/157.6 |
| 6,766,817 B2 | 7/2004 | Da Silva | |
| 6,867,346 B1 * | 3/2005 | Dopps et al. | 604/378 |
| 7,074,301 B2 | 7/2006 | Hamed et al. | |
| 7,094,318 B2 | 8/2006 | Hamed et al. | |
| 2003/0208175 A1 | 11/2003 | Gross et al. | |
| 2004/0177935 A1 | 9/2004 | Hamed et al. | |
| 2005/0045290 A1 | 3/2005 | Hamed et al. | |
| 2005/0079361 A1 * | 4/2005 | Hamed et al. | 428/413 |
| 2005/0245159 A1 | 11/2005 | Chmielewski et al. | |
| 2005/0247419 A1 | 11/2005 | Hamed et al. | |
| 2005/0256470 A1 | 11/2005 | Hamed et al. | |
| 2005/0263258 A1 | 12/2005 | Hamed et al. | |
| 2006/0118258 A1 | 6/2006 | Chmielewski et al. | |
| 2006/0184147 A1 | 8/2006 | Hamed | |
| 2007/0020452 A1 | 1/2007 | Hamed et al. | |

* cited by examiner

LIQUID DISTRIBUTION MAT MADE OF ENHANCED CELLULOSIC FIBERS

BACKGROUND

1. Field of the Art

The various embodiments described herein relate generally to enhanced cellulosic fibers having a modified morphology suitable for use in a liquid distribution mat in an absorbent article. The mat made thereof has enhanced vertical wicking properties. When used in an absorbent article such as a baby diaper, the mat rapidly acquires and transports bodily discharges from the point of insult to other regions of the absorbent article, thereby maximizing the utilization of an absorbent structure.

2. Description of Related Art

Cellulose fibers are well known and are used in a wide variety of disposable absorbent articles such as diapers, incontinence products, and feminine hygiene products. Disposable absorbent articles typically are made with an absorbent core made of a composite of cellulosic fluff pulp and superabsorbent polymer sandwiched between a liquid pervious top sheet, and a liquid impervious backsheet. An optional fluid distribution layer may be disposed between the top sheet and the absorbent core or between the back sheet and the absorbent core. The distribution layer may include a wide variety of materials, including, for example, cellulosic fiber, synthetic fiber, or a mixture of both.

Distribution layers typically are made by a wet-laid process, because wet-laid materials typically possess excellent tensile strength in the wet and dry states and high vertical liquid wicking. "Vertical wicking" as used herein refers to the ability of a material to draw fluids in a vertical direction against gravity. Vertical wicking is a desirable property since it indicates a material's ability to move fluid away from the point of contact, allowing more complete utilization of the absorbent article. As a result, a wearer of the absorbent article is left with a drier feel to the skin.

Several approaches for making a liquid distribution layer have been reported in the literature. Examples of liquid distribution layers include cellulosic foams, such as those commercially available from Spontex SA. France, or High Internal Phase polymerized materials such as those described in U.S. Pat. No. 5,268,224 (DesMarais), the disclosure of which is incorporated herein by reference, in its entirety. In an alternative approach, high surface area synthetic fibers have been applied in absorbent structures in order to improve the liquid distribution, such as described in U.S. Statutory Invention Registration No. H1511, the disclosure of which is incorporated herein by reference, in its entirety.

Other exemplary liquid distribution layers include cellulosic-fiber based materials, such as those disclosed in U.S. Pat. No. 3,575,174 and U.S. Pat. No. 4,781,710, the disclosures of which are incorporated herein by reference, in their entirety. In these materials, portions of the structure are compressed to a higher density, such as along "wicking lines" or in closed mesh patterns. These compressed portions have smaller pores that have increased wicking height. The creators of these materials also aimed at achieving a certain preferential fluid distribution direction. However, in these approaches the size of the large pores was reduced so much that the positive impact of the increased wicking height was counterbalanced by reduced amount of fluid which could be transported to such heights. Another approach to altering the pore size of distribution materials is described in U.S. Pat. No. 5,244,482 (the disclosure of which is incorporated herein by reference, in its entirety), in which reducing the maximum pore size of a fibrous structure containing meltable fibers is accomplished by stretching the fibrous structure in one direction and "freezing" the deformation by heat curing the fibers.

Other material composites have been developed that allowed for a more tailored pore size and pore size distribution. Exemplary materials are described in U.S. Pat. Nos. 5,549,589 and 5,800,416 (the disclosures of which are incorporated herein by reference, in their entirety), which provide a resilient structure made of specially stiffened cellulosic fibers, such as cross-linked cellulose fibers, in which the large pores of the structure are filled in with small and thin cellulosic fibers such as eucalyptus fibers. In both patents, thermoplastic fibers and chemical binders are added to the materials to provide sufficient integrity and strength to the material.

However, the aforementioned approaches are complex to manufacture and, hence, are relatively expensive. In addition, these technologies are still limited by the inverse relationship of wicking height and wicking flux, i.e. wicking height can be increased, but at cost of reduced wicking flux. As used herein, "wicking flux" relates to the amount of fluid being transported vertically through a certain cross-section of a distribution structure to a given height in a predetermined amount of time.

The description herein of certain advantages and disadvantages of known liquid distribution fibers and webs for use in absorbent articles, and methods of their preparation, is not intended to limit the scope of the embodiments described herein. Indeed, the embodiments may include some or all of the methods and materials described above without suffering from the same disadvantages.

SUMMARY

In view of the foregoing difficulties and drawbacks, there remains a need in the art for a simple, commercially feasible method for making a high performance liquid distribution mat. There also exists a need for a liquid distribution mat that can be manufactured on a commercial scale, at a relatively low cost. A need also exists for absorbent article comprising a liquid distribution mat that efficiently acquires and distributes liquid throughout the article on successive liquid insults.

A purpose of the embodiments described herein is to fulfill these needs and to provide further related benefits. The embodiments described herein generally are related to a liquid distribution mat that is a wet-laid mat made of enhanced cellulosic fibers that are cellulosic fibers cross-linked in sheet form. The liquid distribution mat also is soft, flexible, and has a high structural integrity in the wet and dry states. The liquid distribution mat also has high absorption and low retention fluid properties coupled with a high vertical wicking properties.

Various embodiments are directed to a method of making a liquid distribution mat from the enhanced fibers. The method involves providing a sheet of enhanced fibers, defiberizing the sheet of enhanced fibers, forming a suspension of the enhanced fibers, and converting the suspension into a wet-laid three-dimensional liquid distribution mat.

In another embodiment, a one-step process is provided for making a liquid distribution mat and the enhanced fibers at the same time. In this embodiment, the method includes providing a sheet of cellulosic base fibers, defiberizing the sheet of the cellulosic fibers, applying a treatment composition containing a cross-linking agent and a catalyst to the fibers, forming a wet-laid three-dimensional structure therefrom, and drying and curing the structure.

As provided in other embodiments, the enhanced fibers and liquid distribution mats of the embodiments may be used in absorbent articles.

These and other objects, features and advantages of the embodiments will appear more fully from the following detailed description of the preferred embodiments.

BRIEF DESCRIPTION OF THE DRAWINGS

The embodiments presented herein can be understood more completely by reading the following detailed description, in conjunction with the accompanying drawings, in which.

DETAILED DESCRIPTION OF PREFERRED EMBODIMENTS

Embodiments presented herein relate generally to enhanced cellulosic fibers with modified morphology suitable for making a liquid distribution mat for an absorbent article. The enhanced fibers impart moderate bulk and resilience to the liquid distribution mat and provide the mat with a generally open structure that rapidly absorbs a liquid from the point of insult and rapidly transports away from the point of insult. Liquid distribution mats including these enhanced fibers are soft and flexible, and have good wet and dry strength. As described in more detail below, the liquid distribution mats of the embodiments have excellent "vertical wicking" properties—i.e., the ability to quickly transport fluid through its structure in a direction opposite to gravitational force. The liquid distribution mat ideally is suited for use in absorbent garment intended for body fluid management, because it allows for greater utilization of the absorbent core in an absorbent garment, and provides a wearer of the absorbent garment a drier feel to the skin.

The liquid distribution mat made in accordance with the embodiments can be advantageously incorporated into a variety of absorbent articles such as diapers and training pants; feminine care products including sanitary napkins and pant liners; adult incontinence products; bed pads; wipes; toweling; surgical and dental sponges; bandages; food tray pads; and the like. The particular construction of the absorbent article is not critical to the present embodiments, and any absorbent article can benefit from these embodiments. Suitable absorbent articles are described, for example, in U.S. Pat. Nos. 5,281,207, and 6,068,620, the disclosures of each of which are incorporated by reference herein in their entirety including their respective drawings. Some of the embodiments described herein provide, as an exemplary structure, a diaper for an infant, however this is not intended to limit the embodiments. The embodiments will be understood to encompass, without limitation, all classes and types of absorbent products and garments, including those described herein.

As used herein, the terms and phrases "absorbent garment," "absorbent article" or simply "article" or "garment" refers to mechanisms that absorb and contain fluids such as body fluids and other body exudates. More specifically, these expressions refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

Throughout this description, the term "disposed" and the expressions "disposed on," "disposed above," "disposed below," "disposing on," "disposed in," "disposed between" and variations thereof are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

As used herein, the phrase "wicking" or "liquid transport" refers to the ability of the distribution mat to draw fluids away from the point of insult to other regions in the absorbent article. "Horizontal wicking" or liquid transport in a "horizontal" direction indicates transport of liquid in the horizontal direction of the material, such as the transverse or longitudinal directions of the web. As used herein, the expression "vertical wicking" refers to the ability of the distribution structure to draw fluids in a vertical direction, i.e., against gravity. Higher vertical wicking values indicate greater liquid transport ability.

Throughout this description, the term "impregnated" insofar as it relates to a treatment composition impregnated in a fiber, denotes an intimate mixture of treatment composition and cellulosic fiber, whereby the treatment composition may be adhered to the fibers, adsorbed on the surface of the fibers, or linked via chemical, hydrogen or other bonding (e.g., Van der Waals forces) to the fibers. "Impregnated" in the context of the embodiments described herein does not necessarily mean that the treatment composition is physically disposed beneath the surface of the fibers.

As used herein, the expressions "sheet form" or "roll form" refer to cellulosic fiber sheets formed using a wet-laid process. The sheets typically have a basis weight of about 200 to about 800 gsm and density of about 0.3 g/cc to about 1.0 g/cc. The pulp sheets are subsequently defiberized in a hammermill to convert them into fluff pulp before being used in an absorbent product. Pulp sheets can be differentiated from tissue paper or paper sheets by their basis weights. Typically, tissue paper has a basis weight of from about 5 to about 50 gsm and paper sheets have basis weights of from about 47 to about 103 gsm, both lower than that of pulp sheets.

As used herein, the phrases "mat" and "wet-laid mat" refer to cellulosic fiber webs that typically have a basis weight of about 80 to about 400 gsm, and a density of about 0.05 g/cc to about 0.15 g/cc. A mat generally is formed of cellulosic fibers that have previously been defiberized, and then formed into a web using a wet-laying process, as described herein.

Various embodiments described herein provide enhanced cellulosic fibers with modified morphology. As used herein, the expression "enhanced fiber" or "fiber with modified morphology" refers to a cellulosic fiber prepared in accordance with the embodiments described herein, that is suitable for use in a liquid distribution mat. Preferably, the enhanced fibers impart moderate bulk and resilience to the mat and provide the web with a generally open structure that rapidly absorbs a liquid from the point of insult and transports it over a large area in the absorbent article.

Figure 1:
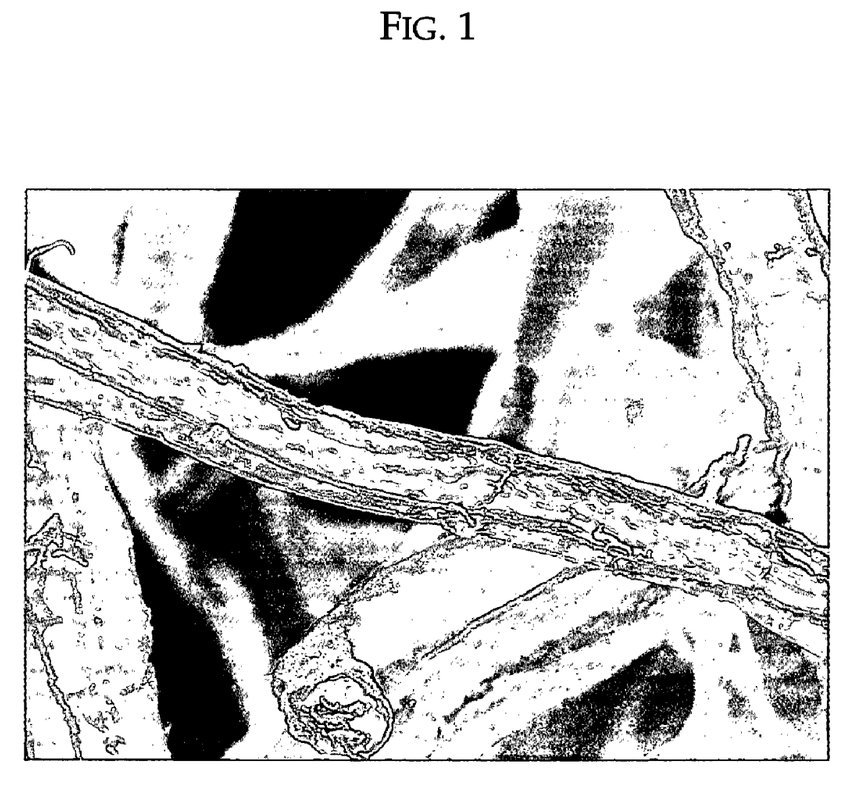
FIG. 1 is a photograph at 500× magnification of a cellulosic fiber cross-linked in sheet form.

The enhanced cellulosic fibers of the embodiments differ from commercially available cross-linked fibers in several ways. First, the enhanced cellulosic fibers are cross-linked in sheet form, rather than individualized form, which is how conventional cross-linked fiber is cross-linked. Because of this, the enhanced fiber is not significantly curled or twisted in any manner-rather, it is stiff and linear as shown in FIG. 1, which is a photograph of a linear cellulosic fiber that has been cross-linked in sheet form. Other exemplary linear fibers that have been cross-linked in sheet form may be found in U.S. patent application Ser. No. 10/683,164 (Publication No. US 2005-0079361 A1), filed on Oct. 14, 2003 by Othman Hamed, et al., which is incorporated by reference herein in its entirety.

Second, the enhanced fiber of the embodiments has low relative cross-linking density. The enhanced fiber is made using 4.5 wt % or less cross-linking agent, as compared to conventional cross-linked fiber that usually is made using greater than 6.0 wt % cross-linking agent. As a result, the enhanced fiber is stiffened to a lesser degree than conventional cross-linked fiber.

Third, the enhanced fiber has fiber lengths and kink angles that are similar to conventional base fiber (e.g., Rayfloc®-JLD-E wood fluff pulp, commercially available from Rayonier, Inc., Jesup, Ga.). The enhanced fiber of the various embodiments preferably has a fiber length of more than 0.5 mm, a kink angle of less than 55°, and kinks per mm of less than 1.0. More preferably the enhanced fiber has a fiber length of more than 1.0 mm, a kink angle of less than 52°, and kinks per mm of less than 0.9. Even more preferably, the enhanced fiber has a fiber length of more than 1.5 mm, a kink angle of less than 50°, and kinks per mm of less than 0.8.

Various embodiments provide a method of making the enhanced cellulosic fibers with modified morphology. The method includes treating cellulosic base fibers in sheet or roll form with a treatment composition, and drying and curing the treated fibers in sheet form. In accordance with the various embodiments, the treatment composition that is useful in making enhanced fiber in sheet form includes a cross-linking agent and a catalyst. Any cross-linking agent known in the art that is capable of cross-linking the cellulosic fibers can be used in the treatment composition of the embodiments described herein. Suitable cross-linking agents include, for example, alkane polycarboxylic acids, polymeric polycarboxylic acids, aldehydes, and urea-based derivatives. Suitable alkane polycarboxylic acids include, for example, aliphatic and alicyclic polycarboxylic acids containing at least two carboxylic acid groups. The aliphatic and alicyclic polycarboxylic acids could be either saturated or unsaturated, and they might also contain other heteroatoms such as sulfur, nitrogen or halogen. Examples of suitable polycarboxylic acids include: 1,2,3,4-butanetetracarboxylic acid, 1,2,3-propanetricarboxylic acid, oxydisuccinic acid, citric acid, itaconic acid, maleic acid, tartaric acid, glutaric acid, iminodiacetic acid, citraconic acid, tartrate monosuccinic acid, benzene hexacarboxylic acid, cyclohexanehexacarboxylic acid, maleic acid, and any combinations or mixtures thereof.

Suitable polymeric polycarboxylic acid cross-linking agents include, for example, those formed from monomers and/or co-monomers that contain carboxylic acid groups or functional groups that can be converted into carboxylic acid groups. Such monomers include, for example, acrylic acid, vinyl acetate, maleic acid, maleic anhydride, carboxy ethyl acrylate, itanoic acid, fumaric acid, methacrylic acid, crotonic acid, aconitic acid, tartrate monosuccinic acid, acrylic acid ester, methacrylic acid ester, acrylic amide, methacrylic amide, butadiene, styrene, or any combinations or mixtures thereof.

Examples of suitable polymeric polycarboxylic acids include polyacrylic acid and polyacrylic acid copolymers such as, for example, poly(acrylamide-co-acrylic acid), poly(acrylic acid-co-maleic acid), poly(ethylene-co-acrylic acid), and poly(1-vinylpyrolidone-co-acrylic acid), as well as other polyacrylic acid derivatives such as poly(ethylene-co-methacrylic acid) and poly(methyl methacrylate-co-methacrylic acid). Other examples of suitable polymeric polycarboxylic acids include polymaleic acid and polymaleic acid copolymers such as, for example, poly(methyl vinyl ether-co-maleic acid), poly(styrene-co-maleic acid), and poly(vinyl chloride-co-vinyl acetate-co-maleic acid). The representative polycarboxylic acid copolymers noted above are commercially available in various molecular weights.

Suitable aldehyde cross-linking agents include, for example, formaldehyde, glyoxal, glutaraldehyde, glyoxylic acid and glyceraldehydes. Suitable urea-based derivatives for use in the embodiments include, for example, urea based-formaldehyde addition products, such as, for example, methylolated ureas, methylolated cyclic ureas, methylolated lower alkyl cyclic ureas, methylolated dihydroxy cyclic ureas, dihydroxy cyclic ureas, and lower alkyl substituted cyclic ureas. Especially preferred urea-based crosslinking agents include dimethyldihydroxy urea (DMDHU, or 1,3-dimethyl-4,5-dihydroxy-2-imidazolidinone), dimethyloldihydroxyethylene urea (DMDHEU, or 1,3-dihydroxymethyl-4,5-dihydroxy -2-imidazolidinone), dimethylol urea (DMU, or bis[N-hydroxymethyl]urea), dihydroxyethylene urea (DHEU, or 4,5-dihydroxy-2-imidazolidinone), dimethylolethylene urea (DMEU, or 1,3-dihydroxymethyl-2-imidazolidinone), and dimethyldihydroxyethylene urea (DDI, or 4,5-dihydroxy-1,3-dimethyl-2-imidazolidinone). Other suitable substituted ureas include glyoxal adducts of ureas, polyhydroxyalkyl urea disclosed in U.S. Pat. No. 6,290,867, and hydroxyalkyl urea and β-hydroxyalkyl amide disclosed in U.S. Pat. No. 5,965,466.

Alternatively, a cross-linking agent suitable for use in the embodiments may be comprised of any combination or mixture of two or more of the above mentioned cross-linking agents.

The treatment composition preferably includes a catalyst to accelerate the reaction between hydroxyl groups of cellulose and cross-linking agent functional groups. Any catalyst known in the art to promote the formation of a covalent bond between hydroxyl group of cellulose and carboxylic acid group or aldehyde group of cross-linking agent may be used. Suitable catalysts for use in the embodiments include alkali metal salts of phosphorous containing acids such as alkali metal hypophosphites, alkali metal phosphites, alkali metal polyphosphonates, alkali metal phosphates, and alkali metal sulfonates. A particularly preferred catalyst is sodium hypophosphite. The catalyst can be applied to the fiber as a mixture with the treatment composition, before the addition of the treatment composition, or after the addition of treatment composition to the cellulosic fiber. The catalyst is preferably used in an amount range from about 1.0 to about 50 weight percent cross-linking agent, more preferably form about 5.0 to about 30 weight percent cross-linking agent, and most preferably form about 10.0 to about 20 weight percent.

The treatment composition may be prepared by any suitable and convenient procedure. For example, the treatment composition may be prepared as an aqueous solution. Preferably the cross-linking agent is present in the treatment composition in a concentration of about 0.5 weight % to about 50.0 weight %, based on the total weight of the composition.

Preferably, the pH of the treatment composition is adjusted to from about 2.0 to about 5.0, more preferably from about 2.5 to about 3.5. The pH can be adjusted using alkaline solutions such as, for example, sodium hydroxide or sodium carbonate.

The cellulosic base fiber used in the embodiments may be any conventional or other cellulosic fiber, so long as it is capable of providing an enhanced fiber having the physical characteristics of the fibers described herein. Suitable cellulosic fibers for use in forming the enhanced fiber of the embodiments include those primarily derived from wood pulp. Suitable wood pulp can be obtained from any of the conventional chemical processes, such as the Kraft and sulfite processes. Preferred fibers include those obtained from various soft wood pulp such as Southern pine, White pine, Caribbean pine, Western hemlock, various spruces, (e.g. Sitka Spruce), Douglas fir or mixtures and combinations thereof. Fiber obtained from hardwood pulp sources, such as gum, maple, oak, eucalyptus, poplar, beech, and aspen, or mixtures and combinations thereof also can be used in the embodiments. Other cellulosic fiber derived from cotton linter, bagasse, kemp, flax, and grass also may be used in the embodiments. The cellulosic base fiber can be comprised of a mixture of two or more of the foregoing cellulosic pulp products. Particularly preferred fibers for use in forming the acquisition fiber of the embodiments are those derived from wood pulp prepared by the Kraft and sulfite-pulping processes. In addition, the cellulosic base fiber may be non-bleached, partially bleached or fully bleached cellulosic fiber.

The cellulosic base fibers can be provided in any of a variety of forms. For example, one aspect of the embodiments contemplates using cellulosic base fibers in sheet or roll form. In another embodiment, the fiber can be provided in a mat of non-woven material. Fibers in mat form are not necessarily rolled up in a roll form, and typically have a density lower than fibers in sheet form. In yet another feature of an embodiment, the cellulosic base fiber is provided in a wet or dry state. It is preferred that the cellulosic base fibers be provided dry in a roll form.

The cellulosic base fiber that is treated in accordance with various embodiments while in the sheet form can be any of wood pulp fibers or fiber from any other source described previously. In one embodiment, suitable cellulosic base fibers in the sheet form are caustic-treated fibers. Preferred caustic-treated fiber is fiber treated with less than 10 weight % caustic. An exemplary caustic-treated fiber is, caustic extractive pulp commercially available as Porosanier-J-HP, available from Rayonier Performance Fibers Division (Jesup, Ga.), and Buckeye's HPZ products, available from Buckeye Technologies (Perry, Fla.).

Any method of applying the treatment composition to the fiber in sheet form may be used, so long as it is capable of providing an effective amount of treatment composition to the fiber to produce the acquisition fiber described herein. Preferably, the application method provides about 10% to about 100% by weight of treatment composition to the fiber, based on the total weight of the fiber. Acceptable methods of application include, for example, spraying, dipping, rolling, impregnating or applying with a puddle press, size press or a blade-coater. Preferably, the fiber is impregnated with an aqueous treatment composition solution. Impregnation typically creates a uniform distribution of treatment composition on the sheet and provides better penetration of treatment composition into the interior part of the sheet. Preferably, the treatment composition is applied to the cellulosic fibers to provide about 0.5% to about 4.5% by weight, and more preferably about 1% to about 4% by weight of cross-linking agent on fiber, based on the total weight of the fiber. By way of example, 3 weight % of cross-linking agent is equal to 3 grams of cross-linking agent per 100 grams fibers.

In one embodiment, a sheet of cellulose fibers in roll form is conveyed through a treatment zone where the treatment composition is applied on both surfaces by conventional methods such as spraying, dipping, slot coating or any other manner of impregnation. A preferred method of applying the treatment composition solution to the fiber in roll form is by puddle press or size press.

In one embodiment, after the treatment composition is applied, the fiber in sheet or roll form then is preferably transported by a conveying device such as a belt or a series of driven rollers to the drying and curing process. For example, the sheet or roll of fiber may be transported through a drying oven and then through a curing oven, such as a forced draft oven. Such drying and curing removes water from the fiber, thereupon inducing the formation of a linkage between hydroxyl groups of the cellulosic fibers and cross-linking agent. Any drying and curing temperature and time can be used so long as they produce the desired effects described herein. Using the present disclosure, persons having ordinary skill in the art can determine suitable drying and curing temperatures and times, depending on the type of fiber, the type of treatment of the fiber, and the desired bonding density of the fiber.

After treatment with the solution of the treatment composition, the fiber preferably is dried and cured in a two-stage process, and more preferably dried and cured in a one-stage process. For example, in one embodiment, the cellulosic fiber is dried and cured in a one-step process, for a period of time ranging from about 3 minutes to about 15 minutes at temperatures within the range of 130° C. to about 225° C. In an alternative embodiment, the drying and curing is conducted in a two-step process. In this embodiment, in the drying step dries the impregnated cellulosic fiber and the dried cellulose fiber then is cured to form intra-fiber bonds. In the embodiment in which the curing and drying are carried out in a two-step process, the drying step is carried out at a temperature below the curing temperature (e.g., between room temperature and about 150° C.) before the curing step. The curing step is then carried out, for example, for about 1 to 10 minutes at a temperature within the range of 150° C. to about 225° C.

In one preferred embodiment, the enhanced fiber is treated with a brightness enhancing agent. Cellulosic fibers treated with conventional cross-linking agent(s) and exposed to high temperatures for curing (typically around 195° C. for 10-15 minutes) tend to develop some discoloration and a burnt-like odor. It is believed that treating the fiber with a brightness enhancing agent can reduce these undesirable effects. Suitable brightness enhancing agents include oxidizing agents used in wood pulping and bleaching processes such as for example, hydrogen peroxide, chlorine dioxide, peracetic acid, perbenzoic acid, chlorine, chlorine dioxide, ozone, sodium hypochlorite and any combination thereof. Preferably, the brightness enhancing agent seemingly performs dual functions: it enhances the pulp brightness by reducing the yellowing, and it removes the burnt-like odor.

Preferably, the brightness enhancing agent is applied to the acquisition fiber in an aqueous solution to provide about 0.001 weight % to about 1.0 weight % of the agent to the fiber, based on the weight of the fiber. More preferably, the agent is applied to provide about 0.005 wt % to about 0.5 wt %, and most preferably to provide about 0.01 wt % to about 0.40 wt % based on the weight of the fiber.

The brightness enhancing agent may be applied to enhanced fiber in sheet form in any of a number of ways, including impregnating, spraying, rolling, slot coating or printing. One exemplary embodiment involves spraying the brightness enhancing solution onto defiberized enhanced fibers. Another exemplary embodiment involves spraying a solution containing the brightness enhancing agent onto enhanced fibers in sheet form immediately after curing.

According to various embodiments, the enhanced fibers may be used to make a liquid distribution mat. When used in a liquid distribution mat, the enhanced fibers provide many advantages over other fibers used for making distribution structures. For example, as discussed above, the enhanced fibers are linear, rather than curled or twisted like conventional cross-linked fibers (e.g., STCC, developed by the Weyerhaeuser Company, Federal Way, Wash.). The twisted nature of conventional cross-linked fiber makes it difficult to form a uniform wet-laid structure. The cross-linked fibers tend to flocculate in an aqueous suspension, forming loose fiber clumps and agglomerations. For this reason, when wet-laid, conventional cross-linked fibers usually are blended with conventional cellulose fibers to produce a more uniform mat. In contrast, the enhanced fibers of the embodiments can be used to produce a uniform wet-laid mat, without the need for a second fiber to provide uniformity.

In addition, a liquid distribution mat including enhanced fibers generally has good wet and dry tensile strength, so that the use of a wet-strength agent is optional or can be used in less than 1.0 wt % based on the total weight of the fiber. The enhanced fibers are particularly advantageous in providing a distribution mat that is soft and flexible. The enhanced fibers also provide a distribution mat that has the ability to quickly move acceptable amounts of fluids through its structure in a direction opposite from gravitational force—known as "Vertical Wicking." Good vertical wicking performance is especially desirable when the liquid distribution mat of the embodiments is used in absorbent article intended for body fluid management, because it indicates the ability of the material to more completely utilize the absorbent article and provide the wearer a drier feel to the skin.

Various embodiments provide methods for making a liquid distribution mat from the enhanced fibers. In one exemplary embodiment, the method comprises defiberizing the sheet of enhanced fiber prepared by the embodiments described herein, and the individualized fiber is formed into a liquid distribution mat. The enhanced fiber may be defiberized by any technique known or later-developed in the art, such as, for example, by passing the fiber through a hammermill or by dispersing it in an aqueous medium. Preferably, the sheet of enhanced fiber is defiberized by dispersing the fiber in an aqueous medium. Dispersal in an aqueous medium is preferable because it is a more practical method, and a hammer mill may damage the fiber and increase fine contents. After the enhanced fiber has been defiberized, the resultant individualized fiber is formed into a three-dimensional liquid distribution mat by either a wet-laid or an air-laid process. Because it is desired that the liquid distribution mat of the embodiments should exhibit sufficient structural integrity (as characterized by dry and wet tensile strengths) and enhanced vertical wicking ability, it is preferred that the process used to prepare the liquid distribution mat be prepared by a wet-laid process. As demonstrated in the examples below, a liquid distribution mat prepared by a wet-laid process as described herein, exhibits excellent vertical wicking properties.

The liquid distribution mat of the embodiments can be formed by any suitable wet-laid process known in the art. Sheets of enhanced fibers prepared in accordance with the embodiments described herein generally have higher structural integrity than sheets of untreated cellulosic fibers. Generally, the sheets of enhanced fibers have higher tensile strengths and are more stiff, which makes it more difficult to disperse the sheet in an aqueous medium using conventional pulping apparatus. In one embodiment, forming a liquid distribution mat includes suspending a sheet of enhanced fiber in an aqueous medium. The suspension is then passed through a hydropulper, (e.g., Tornado, Bolton Emerson Americas, Inc., Lawrence, Mass.) where the sheet is dispersed. Any remaining nits or knots, and clumps or agglomerations are then removed by passing the slurry through a refiner (e.g., Beloit DD4000, Beloit Corporation, Dalton, Mass.). After passing the refiner, the pulp slurry becomes suitable for making liquid distribution mat with knots and nits contents of less than 20%, preferably less than 15% and more preferably less than 10%. After the fiber slurry has been prepared, preferably it is transferred to a headbox wherein the fiber is dewatered and deposited into a screen thereby forming a wet-laid structure. The wet-laid structure may then be subjected to a mechanical press to remove excess water. Preferably, the dewatered mat is dried at about 100° C. to 200° C. to form a liquid distribution mat.

In another embodiment, the liquid distribution mat is prepared using a one-step process, combining the steps of forming the enhanced fiber, and the liquid distribution mat. This method includes providing a sheet of conventional cellulosic base fibers, defiberizing the sheet of the cellulosic fibers, applying a treatment composition to fiber, forming a wet-laid three-dimensional mat therefrom, and drying and curing the wet-laid mat to form the liquid distribution mat.

In the one-step process, the cellulosic fiber in sheet form may be defiberized by any technique known or later-developed in the art. For example, the sheet may be defiberized using a hammermill or by dispersing it in an aqueous medium. Preferably, the sheet of cellulosic fiber is defiberized by a hammermill.

In the one-step process, the treatment composition preferably is in an aqueous solution. Preferably the application of treatment composition provides from about 1.0 weight % to about 3.0 weight % cross-linking agent, and 0.1 weight % to about 1.0 weight % catalyst based on the total weight of the fiber. Preferably, the pH of the aqueous solution of treatment composition is adjusted to from about 2.0 to about 5.0, more preferably from about 2.0 to about 4.0, and even more preferably from about 2.5 to about 3.5. The pH can be adjusted using alkaline solutions such as, for example, sodium hydroxide or sodium carbonate.

In the one-step process, after wet-laying, the mat preferably is not pressed and has a wet pick-up of from about 100 weight % to about 400%, more preferably from about 150 weight % to about 300 weight %. By way of example, a 100 weight % wet pick-up means approximately 100.0 grams of treatment composition per 100.0 grams of oven dried cellulosic fibers.

The liquid distribution mat made in accordance with the embodiments preferably has a basis weight from about 80 gsm to about 400 gsm, more preferably from about 100 gsm to about 400 gsm, and even more preferably from about 160 gsm to about 320 gsm. The liquid distribution mat of the embodiments preferably has a density from about 0.05 g/cm$^3$ to about 0.15 g/cm$^3$, more preferably from about 0.08 g/cm$^3$ to about 0.13 g/cm$^3$. The liquid distribution mat of the embodiments preferably has knots and nits contents of less than 20%, more preferably less than 15% and even more preferably less than 10%.

The liquid distribution mat of the embodiments preferably exhibits flexibility and structural integrity to minimize the incidence of tearing or fragmenting during manufacturing, handling, and use. Preferably, the liquid distribution mat of the embodiments has a tensile strength in the wet state that is capable of providing enough integrity to the mat that when a strip of liquid distribution mat with dimensions of approximately 10.0 cm×30.0 cm is fully saturated with fluid and clamped and hung vertically, it won't break under its own weight.

It is preferred that a liquid distribution mat of the embodiments, having a basis weight of about 320 gsm, exhibits a dry tensile strength that is at least about 8.0 N/5 cm. Preferably, the liquid distribution mat has a wet tensile strength that is at least about 5 N/5 cm. Wet and dry tensile strengths are measured according to Test Method ASTM 828-93, modified so that the tensile tester has a 3-inch jaw width, a jaw span of 4 inches, and a crosshead speed of 1.0 inches per minute. Preferably, the liquid distribution mat of the embodiments has a ratio of wet tensile strength to dry tensile strength of about 0.7 to about 0.9.

Preferably, the liquid distribution mat of the embodiments has a tensile index of about 0.3 Nm/g to about 1.0 Nm/g, more preferably about 0.5 Nm/g. Tensile index is calculated by dividing tensile strength (N/m) by the basis weight of the mat (g/m$^2$ or gsm).

If desired, a wet strength agent may optionally be added to the fibers forming a liquid distribution mat to improve structural integrity of resulting liquid distribution mat in the wet state. As used herein, the phrase "wet strength agent" refers to a material that stabilizes fiber-to-fiber bonding, thereby make the liquid distribution web resistant to disruption in the wet state. In this instance, the wet state usually will mean when the product is largely saturated with water or other aqueous solutions, but could also mean significant saturation with body fluids such as urine, blood, mucus, menses, runny bowel movement, lymph and other body exudates. Preferably, the wet strength agent is sufficiently hydrophilic so that the resin does not adversely affect the liquid distribution property of the mat.

The wet strength agent may be applied to the enhanced fiber of the embodiments by any method known in the art including, for example, direct addition to a fibrous slurry, such as by injection of the additive into a slurry prior to entry in the headbox. Another exemplary method includes dipping the liquid distribution mat into a solution of the wet-strength agent, pressing the dipped mat to remove excess solution, and drying the web. Yet other methods of applying the wet-strength agent to the enhanced fiber includes spraying, rolling, slot coating or printing. It should be noted that application of a wet-strength agent to the enhanced fiber is not limited to application in solution, and can also include application in an emulsion, suspension or dispersion thereof.

Preferably, a solution of wet-strength agent is applied to the enhanced fiber during the wet-laying process. Levels of the wet-strength agent retained in the fibers after wet-laying and pressing preferably range from about 0.05 weight % to about 5 weight %, based on the weight of the dried fibers. In one embodiment, the wet-strength agent may be retained in the fibers in levels from about 0.1% to about 2.5% by weight of the fibers. In another embodiment, the wet-strength agent is retained in the fibers in levels from about 0.25 weight % to about 1.0 weight % based on the weight of the fibers.

Suitable wet strength agents include polyamine-amide epichlorohydrin compounds, such as those available under the Kymene® label from Hercules, Inc. of Wilmington, Del. (e.g., Kymene 557H); and polymeric aldehyde-functional compounds, such as PAREZ 631 NC available from Cytec Industries of West Patterson, N.J.; chloroxylated polyacrylamides; and HERCOBOND 1366, manufactured by Hercules, Inc. of Wilmington, Del. Another examplary wet strength agent is glyoxylated polyacrylamide, such as PAREZ 745, which is a glyoxylated poly (acrylamide-co-diallyl dymethyl ammonium chloride). Other wet strength agents suitable for use in the embodiments include urea formaldehyde and melamine formaldehyde resins, and polyethylenimine resins.

The liquid distribution mat may be characterized by vertical wicking properties—i.e., the ability of the mat to wick fluid in a direction opposite to gravitational force. Preferably, the liquid distribution mat is able to wick the aqueous liquid to the height required within a reasonable period of time. Good vertical wicking performance is especially desirable when the liquid distribution mat is used in an absorbent article, because the liquid distribution mat must be able to quickly and efficiently move fluid away from the point of insult (e.g., the crotch) to other areas of the absorbent article before the next insult occurs.

One measure of the liquid distribution mat's vertical wicking performance is the Vertical Wicking Height—i.e., the distance that the mat can wick fluid in a direction opposite to gravitational force. The liquid distribution mat of the embodiments preferably exhibits a Vertical Wicking Height of 15 cm in less than 3 minutes, more preferably in less than 2.5 minutes, and even more preferably in less than 2.0 minutes.

Preferably, the liquid distribution mat absorbs and wicks a sufficient amount of liquid per gram of the mat so as to have a liquid flux adequate to substantially move the liquid out of the insult area prior to the next liquid insult. Thus, another measure of the liquid distribution mat's vertical wicking performance is the Vertical Wicking Absorbent Capacity (VWAC)—i.e., the amount of fluid wicked per gram of the mat, in each 1.0 inch vertical segment of the mat (see test method in Example 4). Preferably the liquid distribution mat of the embodiments exhibits at a vertical height of 2 inches, a VWAC of about 6.0 g saline/g, more preferably about 8.0 g saline/g, and even more preferably about 10.0 g/g. Preferably the liquid distribution mat of the embodiments exhibits at a vertical height of 4 inches, a VWAC of about 5.0 g saline/g, more preferably about 6.0 g/g, and even more preferably about 7.0 g/g. The liquid distribution mat of the embodiments preferably exhibits at a vertical height of 8 inches a VWAC of about 3.0 g saline/g, more preferably about 4.0 g saline/g, and even more preferably about 5.0 g/g. The liquid distribution mat of the embodiments preferably exhibits at a vertical height of 12 inches a VWAC of about 1.0 g saline/g, more preferably about 2.0 g saline/g, and even more preferably about 3.0 g/g.

Vertical Wicking Rate (VWR) is a measure of the speed at which the liquid distribution mat is able to move fluid a predetermined distance in a direction opposite to gravitational force (see test method in Example 4). Preferably, within 10 seconds the liquid distribution mat of the embodiments wicks 6.0 g of saline to a 5 cm height, more preferably it wicks 7.0 g of saline to a 5 cm height, and even more preferably 8.0 g of saline to a 5 cm height. Preferably, in not more than 230 seconds the liquid distribution mat of the embodiments wicks 20.0 g of saline to a height of 20 cm, more preferably it wicks 22.0 g of saline to a height of 20 cm, and even more preferably it wicks 25.0 g of saline to a height of 20 cm. Preferably the liquid distribution mat vertically wicks saline to a height of 20 cm in about 3 to about 8 minutes, more preferably from about 3 to about 7 minutes, and even more preferably from about 4 to about 6 minutes.

Other vertical wicking characteristics include the Vertical Absorption Height (VAH) and Vertical Desorption Height (VDH). These two properties are indicate the ability of the liquid distribution mat to resist wet collapse and maintain a sufficient pore structure, thus allowing fluid to continue moving through the mat. When used in an absorbent article, it is important for the distribution mat to function very well in multiple insult situations to move the acquired liquid rapidly to other liquid storage components of the absorbent structure.

Vertical Absorption Height is a measure of the height at which the vertical absorbent capacity is 50% of the free absorbent capacity under equilibrium conditions at 22° C. Vertical Desorption Height refers to the mat's ability to hold onto liquid at various heights at equilibrium conditions at 22° C. The VDH is determined by draining (via gravity) a sufficiently long strip of the liquid distribution mat previously saturated with saline solution. For the purposes of the present invention, the VDH of interest is at the height at which the vertical absorbent capacity is 50% of the free absorbent capacity under equilibrium conditions at 22° C. The test methods for determining VAH and VDH are provided in Example 4 below. For more details on these properties see [P. K. Chatterjee and H. V. Nguyen in "Absorbency," Textile Science and Technology, Vol. 7; P. K. Chatterjee, Ed.; Elsevier: Amsterdam, 1985; Chapter 2.].

Preferably the liquid distribution mat of the embodiments has a VAH value of greater than about 10 cm, more preferably greater than about 12 cm, and even more preferably more than about 15 cm. The liquid distribution mat preferably has a VDH of not greater than 200% the value of VAH, more preferably not greater than 170%, and even more preferably not greater than 150%.

In addition to the ability to acquire liquids from a point of insult and wick the materials against gravity to other portions of the absorbent article, the liquid distribution mat also must be able to release liquids to the storage component of the absorbent article. One way to characterize the liquid distribution mat's ability to absorb and retain fluid is by measuring its absorbent capacity (CAP) and its centrifuge retention capacity (CRC). The absorbent capacity measures the ability of the fiber to absorb fluid when it is not subjected to a confining or restraining pressure. The centrifuge retention capacity measures the ability of the fiber to retain fluid against a centrifugal force. It is desirable that the liquid distribution mat can absorb large quantities of fluid, but retain very little. Generally speaking, if the liquid distribution mat retains a large amount of liquid, it is not able to release liquid to the storage component, and is not able to wick the liquid away from the point of insult. This can cause the insult point in the absorbent article to remain so heavily loaded with liquid that it would be susceptible to leaking.

Preferably, the liquid distribution mat of the embodiments has a centrifuge retention capacity of less than about 0.70 grams of saline per gram of oven dried (OD) fibers (hereinafter "g/g OD"). More preferably, the liquid distribution mat has a CRC of less than about 0.65 g/g OD, even more preferably less than about 0.60 g/g OD, and even more preferably less than about 0.55 g/g OD. The liquid distribution mat preferably has an absorbent capacity of greater than about 11.0 g/g OD, more preferably has a CAP of greater than about 12.0 g/g OD, even more preferably has a CAP of greater than about 13.0 g/g OD, and even more preferably has a CAP of greater than about 15.0 g/g OD.

Free Volume (FV) is a measure of the pore volume of the mat, i.e., the volume of the openings or cells in the liquid distribution mat per unit mass of fiber that forms the mat. The free volume of the liquid distribution mat affects a number of performance and mechanical features of the liquid distribution mat, such as the vertical wicking capacity, the rate of vertical wicking, and the tensile strength of the mat. A test method for determining free volume of the mat is provided in Example 4 below. While this is one preferred test method, one of ordinary skill in the art will recognize that there are other methods for determining the theoretical or actual pore volume or free volume of a liquid distribution mat, and that the discussion of Free Volume herein is inclusive of any test that can reasonably be expected to give measurements approximating the actual or theoretical pore volume. The liquid distribution mat of the embodiments preferably has a Free Volume of about 5 mL/g to about 12 mL/g, more preferably from about 6 mL/g to about 10 mL/g.

The enhanced fibers and liquid distribution mats of the embodiments may be incorporated into various absorbent articles such as those intended for body waste management. Exemplary absorbent articles include adult incontinent pads, feminine hygiene products, and infant diapers. Such absorbent articles typically have a liquid permeable top sheet, a liquid impermeable back sheet, and an absorbent core (fluid storage layer) disposed between the top sheet and the back sheet. The liquid distribution mat may advantageously be placed in a layer above (between the top sheet and the absorbent core) or below (between the backing sheet and the absorbent core) the absorbent core to aid in the distribution of fluid, to increase the utilization of the materials within the absorbent core. Preferably the liquid distribution mat has dimensions no greater than the absorbent core. More preferably, the liquid distribution layer has an area that is about 30% to about 100% of the total area of the absorbent core, and even more preferably from about 80% to about 100% of the total area of the absorbent core.

In order that the various embodiments of the invention may be more fully understood, they will be illustrated, but not limited, by the following examples. No specific details contained therein should be understood as a limitation to the embodiments except insofar as may appear in the appended claims.

EXAMPLES

Example 1

In this example, enhanced cellulosic fiber was prepared then converted into a liquid distribution mat by wet-laying method.

Preparation of Enhanced Fiber

A treatment composition solution containing citric acid (3.2 weight %), polymaleic acid (PMA, 0.8 weight %), and catalyst sodium hypophosphite (0.8 weight %) was prepared. The pH of the solution was adjusted to about 2.9 to 3.3 with an aqueous solution of NaOH (50 weight %).

The treatment composition solution then used to treat hand sheets of fluff pulp obtained from a jumbo roll of Rayfloc®-J-LDE (conventional wood fluff pulp, commercially available from Rayonier, Inc., Jesup, Ga.). The hand sheets measured 12 inches by 12 inches, had a basis weight of about 680 gsm (g/m$^2$) and a density of about 0.44 g/cc. Each hand sheet was dipped in the treatment composition solution, then pressed to achieve the desired level of treatment composition solution (100% wet pick-up). The treated sheets was then dried and cured at about 186° C. The curing was carried out in an air-driven laboratory oven for about 10 minutes to produce enhanced fibers in sheet form.

Converting Enhanced Fiber Into a Liquid Distribution Mat by Wet-laying

A liquid distribution mat measuring 14 inches×14 inches, and having a basis weight of about 320 gsm was prepared in the following manner: A sheet of enhanced fiber (40.0 g) made as described above was cut into small pieces and added to a 4.0 L blender (Waring Commercial, Torrington, Conn.) filled with about 2.0 liters of distilled water. The blender was run until the fiber was completely dispersed in water (about 90 sec). The contents of the blender were then poured into a handsheet former chamber containing about 10.0 liters of distilled water. More water was then added to the chamber to dilute the fiber to a consistency of about 0.15%. Wet strength agent Kymene® 557H was then added to the suspension in the chamber to provide about 0.5 weight % wet strength agent based on the weight of the fiber. The suspended fibers in the handsheet mold were then gently agitated with a standard perforated mixing plate that was inserted into the slurry and moved up and down about 12 times, then removed. The water was then drained through the forming screen of the handsheet former. The handsheet former was then opened and two layers of blotting paper were placed on the top of the handsheet. A roller, having the equivalent of about 2.3 pounds of pressure per linear inch, was rolled back and forth thrice on each of the left side, the right side, and the center of the formed handsheet. The formed hand sheet, with blotting paper attached, was then lifted off the forming screen. The blotting paper was then peeled off of the handsheet, and the hand sheet was placed in a 125° C. oven until it dried. The handsheet was then removed from the oven and used for evaluation for liquid distribution properties.

Example 2

In this example, enhanced cellulosic fiber was prepared then converted into a liquid distribution mat by wet-laying method.

Preparation of Enhanced Fiber

The method described in Example 1 was followed, except that in this example the treatment composition solution contained 2.0 weight % citric acid, 0.5 weight % polymaleic acid, and 1.0 weight % sodium hypophosphite.

Converting Enhanced Fiber Into a Liquid Distribution Mat by Wet-Laying

Enhanced fiber was first fluffed using hammermill and then converted into a 14 inch by 14 inch liquid distribution mat with a basis weight of about 320 gsm, using the method described in Example 1.

Example 3

In this example, a one-step process for making a liquid distribution mat from enhanced fibers is described.

A 14 inch by 14 inch wet-laid liquid distribution mat with a basis weight of about 320 gsm was made in the following manner: Never dried Rayfloc®-J-LDE (40.0 g) was added to a handsheet former containing an aqueous solution (25.0 L) of citric acid (0.95 wt %), PMA (0.22 wt %), and sodium hypophosphite (0.22 wt %). The pH of the solution was adjusted to about 3.0 by adding sodium hydroxide solution (50%). The suspended fibers in the handsheet mold were then gently agitated with a standard perforated mixing plate that was inserted into the slurry and moved up and down about 12 times, then removed. The water was then drained through the forming screen of the handsheet former. The handsheet former was then opened and the wet-laid mat was left off the screen and placed on a blotting sheet. The wet-laid mat was kept on the blotting sheet until the wet pick-up reached a level of about 3.2 wt % citric acid, 0.22 wt % PMA, and 0.22 wt % sodium hypophosphite. The blotting paper was then peeled off of the handsheet, and the hand sheet was cured in oven at 185° C. for about 12 min. The handsheet was then removed from the oven and used for evaluation for liquid distribution properties.

Absorbent Capacity and Centrifuge Retention Capacity

The enhanced fibers of Examples 1 and 3 were evaluated for absorbent capacity and centrifuge retention capacity, using the test methods provided immediately below.

The test was performed using a plastic cylinder with one inch inside diameter having a 100-mesh metal screen attached to the base of the cylinder. Into the cylinder was inserted a plastic spacer disk having a 1.0 inch diameter and a weighs about 4.4 g, the weight of the cylinder assembly was determined to the nearest 0.001 g ($W_0$). A test sample having a circular shape with a 1 inch was obtained for the liquid distribution mat prepared herein. The sample was placed in the cylinder, the spacer disk then was inserted back into the cylinder on the test sample, and the cylinder assembly was weighed to the nearest 0.001 g ($W_1$).

The cell and its contents then were hanged in a Petri dish containing sufficient amount of saline solution (0.9% by weight NaCl) to touch the bottom of the cell and the fiber was allowed to stay in contact with the saline solution for 10 minutes. Then it was removed and hanged in another empty Petri dish and allowed to drain for one minute, and the weight of the cell and contents was determined ($W_2$). The weight of the saline solution absorbed per gram fibers then was calculated according to the equation below, the result of which was expressed as the "absorbent capacity" (g/g).

$$\text{Absorbent Capacity} = \frac{W_2 - W_1}{W_1 - W_0}$$

The cell then was centrifuged for 3 minutes at 2400 rpm (Centrifuge Model HN, International Equipment Co., Needham HTS, USA), and the weight of the cell and contents is reported ($W_3$). The centrifuge retention capacity was then calculated according to the equation below, the result of which was expressed as the "centrifuge retention capacity" (g/g).

$$\text{Centrifuge Retention Capacity} = \frac{W_3 - W_0}{W_1 - W_0}$$

The test results for the samples of Example 1 and 3 are shown in Table 1 below.

TABLE 1

Absorbent properties of enhanced fibers of Examples 1 and 3

|  | Control[1] | Enhanced Fiber/Example 1 | Enhanced Fiber/Example 3 |
|---|---|---|---|
| Absorbent Capacity (g/g OD) | 11.4 | 15.7 | 14.2 |
| CRC (g/g OD) | 0.93 | 0.57 | 0.66 |

[1]Untreated Rayfloc ®-J-LDE.

Example 4

Various samples of the liquid distribution mat were prepared for testing. The characteristics of the liquid distribution mats are summarized in Table 2. The Free Volume of the samples was determined using the test method described above.

TABLE 2

| Liquid Distribution Mat (LDM) prototype | Method of Preparation | Mat Specifications | | |
|---|---|---|---|---|
| | | Basis Weight (gsm) | Density (g/cc) | Free Volume (cc/g) |
| LDM 1 | Example 1 | 320 | 0.1 | 7.5 |
| LDM 2[1] | See below[1] | 160 | 0.097 | 7.6 |
| LDM 3[2] | Made at paper machine[2] | 320 | 0.1 | 7.1 |
| LDM 4 | Example 3 | 320 | 0.092 | 6.8 |

[1]Enhanced fiber made according to method described in Example 1, except that wet strength resin was replaced with polyester bi-component synthetic fiber T255 (3 weight %) obtained from Invista, Salisbury, NC. Liquid distribution mat made according to method described in Example 2.
[2]Made at Herty foundation (Savannah, GA) using a paper machine equipped with a rotoformer headbox and a through air dryer. Enhanced fiber in roll form was dispersed in water using a hydropulper (Tornado, Bolton Emerson Americas, Inc., Lawrence, MA), passed through a refiner (Beloit DD4000, Beloit Corporation, Dalton, MA), and then wet-laid in the presence of wet strength agent Kymene 557H (0.5 weight %).

Each of the above samples were tested according to the test methods described below.

Free Volume

The Free Volume (FV) of each liquid distribution mat (shown in Table 2, above) was determined by measuring the amount of heptane that can be introduced into a sample of the liquid distribution sample. The test was carried out as follows: A sample of a liquid distribution mat was cut to dimensions of 35 cm×10 cm. The dry weight ($W_d$) of the sample was determined to the nearest 0.001 gram and the sample was immersed in heptane in a glass container and allowed to become saturated. While immersed in the heptane, the sample was tapped a few times to expel air. The sample was kept in contact with the heptane for about 10 minutes then was removed without squeezing heptane out of it. Excess fluid was allowed to drip off of the sample in the flat position for about 30 seconds. At this point, the wet weight ($W_w$) of the sample was measured, in grams. This procedure was repeated for two more samples, recording wet and dry weights of each sample. Free volume (FV, cm³/g) is the volume of heptane (density=0.679 g/cc at 20° C.) in the saturated distribution mat per unit weight of dry mat, calculated according to the following equation:

$$FV(CC/g) = \frac{Wt(g) \text{ of heptane absorbed by the sample}}{Wt(g) \text{ of } LDM \text{ sample} \times 0.679 \text{ g/cc}}$$

The Vertical Wicking Tests

The vertical wicking rate, and vertical wicking height, and total vertical wicking capacity measure the ability of the liquid distribution mat to wick fluid vertically from a reservoir. These properties were determined using the following procedure.

A sample strip of liquid distribution mat was prepared measuring approximately 5 cm wide×30 cm long. The sample strip was supported vertically to a plastic stand using wire net such that the bottom of the sample strip is placed at a height about 2.0 cm below the bottom of the stand. Starting at the free end of the 5 cm wide strip, a first line was marked at 1.0 cm from the edge of the strip, and then consecutive lines at 5 cm intervals were marked along the entire length of the strip. The stand was clamped over a tray positioned on a scale. A 0.9 weight % saline solution, colored with green food coloring, was introduced to the bath. The stand was lowered just enough for the saline solution to contact the bottom of the sample strip. Timing was commenced once the liquid reached the first line (1.0 cm from the strip edge). The liquid was allowed to wick up the strip to its equilibrium height (approximately 30 minutes). The time required for the saline solution to reach each of the marked heights, and the amount of liquid wicked during that time (grams) were recorded. The total amount of liquid wicked during the 30 minute period was measured (in grams). The "total vertical wicking capacity" (TVWC) is the total amount of liquid wicked during the 30 minute period, divided by the weight of the sample.

Table 3 shows the results obtained for prototype LDM 3, described above.

TABLE 3

| Wicking height (cm) | Time (sec) | Fluid wicked (g saline) | TVWC g saline/g LDM |
|---|---|---|---|
| 5 | 8.3 | 8.3 | |
| 10 | 33.5 | 15.3 | |
| 15 | 257 | 21.1 | |
| 25 | 674 | 28.0 | |
| | 30 minutes | | 7.1 |

Vertical Wicking Absorbant Capacity:

For this test, the Vertical Wicking Rate experiment was repeated, the sample strip was marked using a permanent marker before placing it in the liquid reservoir. Starting at one end of the 5 cm width of the strip, a first line was marked at 1.0 cm from the strip edge and then consecutive lines at 1 inch intervals were marked along the entire length of the strip. The liquid was allowed to wick up the strip for 30 minutes, then the sample is quickly removed and cut into a 1 inch segment while held vertically. Each piece is weighed, dried, and then reweighed. The vertical wicking absorbant capacity (VWAC) is calculated for each piece according to the following equation.

$$VWAC(g/g) = \frac{\text{Wet Wt(g) of segment} - (Wt(g) \text{ of segment after drying} - CF)}{Wt(g) \text{ of segment after drying} - CF}$$

Figure 2:
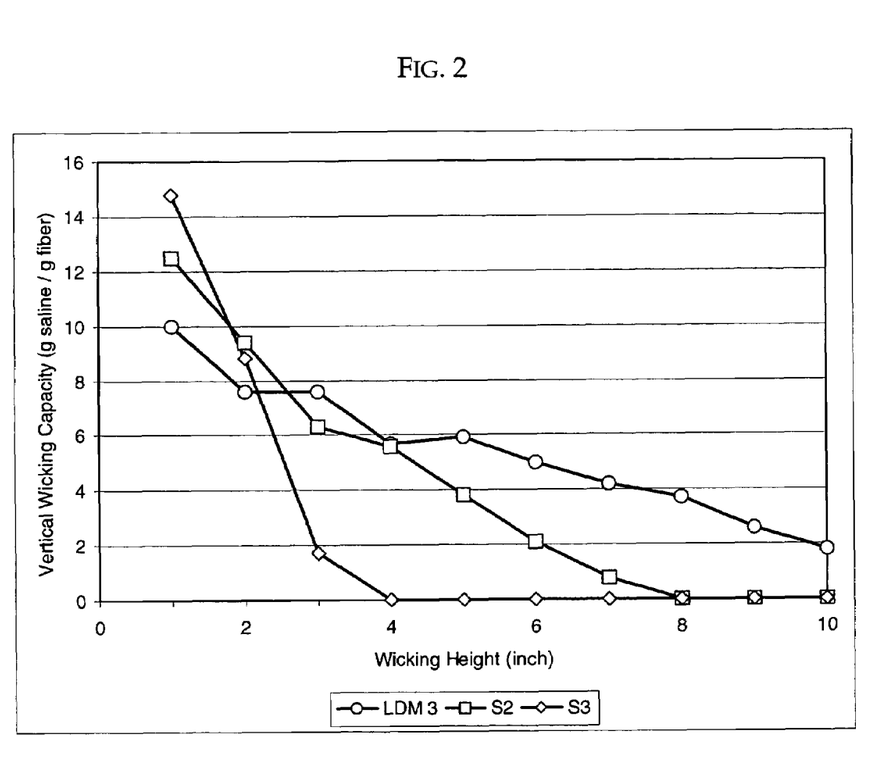
FIG. 2 shows vertical wicking capacity versus vertical wicking height for liquid distribution mat (LDM 3, see Table 2 for specifications), as compared to liquid distribution materials made from commercially-available cross-linked fiber, and conventional cellulosic fibers.

-continued

Where $CF = \dfrac{\text{correction factor}}{\text{(weight of sodium chloride in dried sample)}}$ $= \dfrac{\text{(Wet Wt(g) of segment} - }{\text{Wt(g) of segment after drying)} \times 0.009}$ The vertical wicking capacity for sample LDM 3, as well as for a wet-laid mat of commercially available cross-linked cellulosic fiber (labeled "S2"), and an air-laid mat of commercially available cross-linked cellulosic fiber (labeled "S3") as a function of height are shown in FIG. 2.

The results shown in FIG. 2 indicate that wet laying is a better process for making a liquid distribution mat than an air-laying process. The air-laid structure of S3 structure was only able to wick the fluid to a height of to height of about 4 inches, after which it collapsed.

The results also show that the enhanced fiber forms a wet laid distribution mat with excellent vertical wicking when compared with wet-laid structure S2 made form conventional cross-linked fiber made in individualized form. The S2 structure made from conventional cross-linked fiber collapsed at a height of about 8 inch. In comparison, the wet-laid mat made of the enhanced fiber continued to wick at a height of 10 inches.

Vertical Desorption Height

Figure 3:
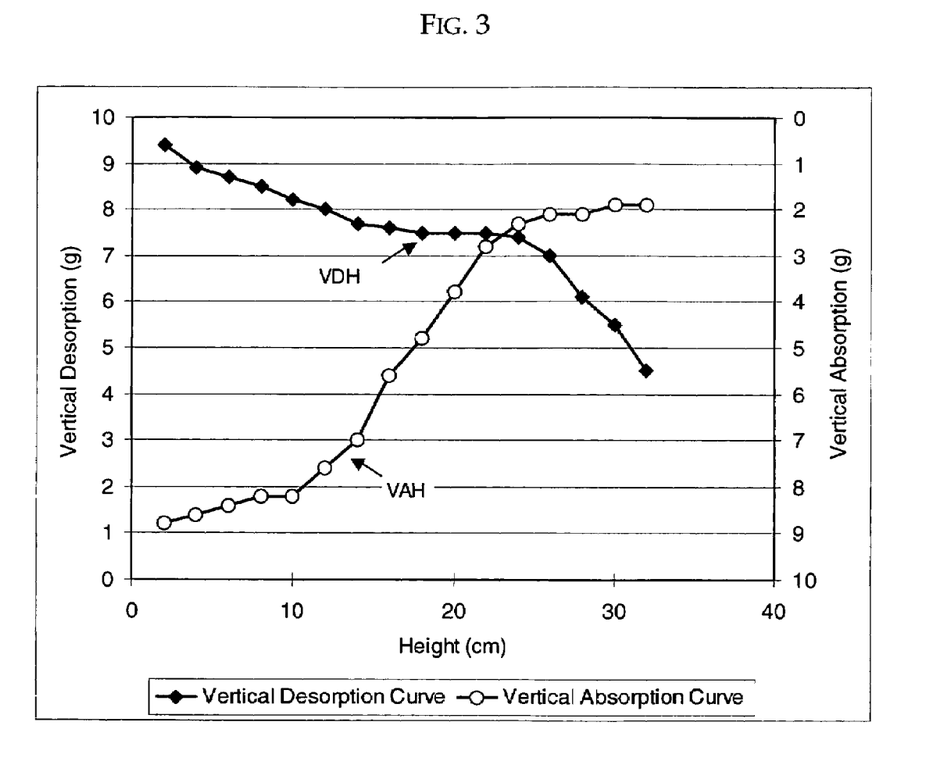
FIG. 3 shows the vertical absorption height and vertical desorption height for a liquid distribution layer (LDM 3, see Table 2 for specifications).

Vertical Desorption Height (VDH) is a measure of a material's ability to hold onto liquid as a function of height. The sample strip of LDM 3 was prepared, having dimensions of 30.0 cm×5.0 cm and a density of about 0.1 g/cc. Starting at one end of the 5 cm width of the strip, a first line was marked at 0.5 cm from the strip edge and then consecutive lines at 2.0 cm intervals were marked along the entire length of the strip. The test strip was saturated in saline 0.9% (optionally containing green food coloring), then positioned vertically such that the lower end is immersed 0.5 cm in a reservoir of saline. The saline was allowed to drain from the sample until equilibrium is reached, about 2.0 hrs. The reservoir was then quickly removed and the strip was cut into 2.0 cm segments after discarding the portion of the sample that was immersed in the reservoir. Each piece was weighed, dried, and then reweighed. The vertical wicking capacity was calculated for each piece.

The Vertical Desorption curve (FIG. 3) was generated by plotting the vertical wicking capacity of each segment as a function of height, using the distance from the top of the fluid reservoir to the midpoint of each segment. The Vertical Desorption Height (marked "VDH" on FIG. 3) is the height at which the vertical wicking capacity is one-half the absorbent capacity of the liquid absorption mat (as determined above).

Vertical Absorption Height

The sample strip of LDM 3 was prepared, having dimensions of 30.0 cm×5.0 cm and a density of about 0.1 g/cc. Starting at one end of the 5 cm width of the strip, a first line was marked at 0.5 cm from the strip edge and then consecutive lines at 2.0 cm intervals were marked along the entire length of the strip. The test strip was positioned vertically such that the lower end is immersed 0.5 cm in a reservoir of saline. The sample was allowed to stay in contact with the saline solution for about 2.0 hrs. The reservoir was then quickly removed and the strip was cut into 2.0 cm segments after discarding the portion of the sample that was immersed in the reservoir. Each piece was weighed, dried, and then reweighed. The vertical wicking capacity was calculated for each piece.

The Vertical Absorption curve (FIG. 3) was generated by plotting the vertical wicking capacity of each segment as a function of height, using the distance from the top of the fluid reservoir to the midpoint of each segment. The Vertical Absorption Height (marked "VAH" on FIG. 3) is the height at which the vertical wicking capacity is one-half the absorbent capacity of the liquid absorption mat (as determined above).

The VAH and VDH were determined for LDM 3, as shown in FIG. 3. The VAH of LDM 3 is about 12 centimeters. At this height, vertical absorption is about 7.5 g, which is about one half of the absorbent capacity shown in Table 1. The VDH is about 17 cm, or about 142% of the VAH. These results indicate that the LDM 3 should be able to maintain a sufficient pore structure and resist wet collapse upon multiple insult situations, as is the case with absorbent articles.

Tensile Tests

Tensile strength measurements of both wet and dry strips obtained from liquid distribution mats were done using SCAN-P58:86 Instron. For each sample, a series of 2.0 inches×6 inches rectangular strips were cut, half of the strips were wetted with saline solution (0.9%) to about 200% wet pick-up. The strips were then individually mounted in the Instron with a 4 inch gage length and a load cell of 10N (load cell is chosen so that peak load results generally fall between about 20 and about 80 percent of the full scale load) with a crosshead speed of 1.00 in/min. The load was applied until the sample ruptured. The tensile strength at the time of rupture was recorded for each strip. The tensile strength measurement was done under the controlled conditions of 70° F. ambient temperature and 52% relative humidity. The tensile strength for dry strips (DTS) and wet strips (WTS) were then used to determine WTS/DTS ratio. The results of this test are shown in Table 4, below.

TABLE 4

| | Tensile Strength (N/5.0 cm) | | |
|---|---|---|---|
| LDM prototype | Dry | Wet | WTS/DTS |
| LDM 1 | 5.5 | 4.7 | 0.85 |
| LDM 2[1] | 7.5 | 6.7 | 0.90 |
| LDM 3 | 5.4 | 4.4 | 0.81 |
| LDM 4 | 9.5 | 9.0 | 0.95 |

[1]Enhanced fiber made according to the method of Example 1, except that wet strength resin was replaced with bi-component synthetic fiber (3 weight %).

The results in Table 4 show that the liquid distribution mats, made of enhanced fibers, maintain their structural integrity even upon saturation with fluid. Although not shown directly, the liquid distribution mats also are able to maintain their structural integrity in a multiple-insult situation.

Acquisition and Rewet

Liquid distribution mat LDM 2 was evaluated for acquisition and rewet performance. The acquisition and rewet test is a useful tool for understanding fluid distribution performance in the x-y plan.

In this test, a diaper was stretched out flat and a weighted apparatus (0.1 psi load), into which a tube of specific diameter was inserted, was placed on top of the diaper. Fluid (100 mL 0.9% saline) was poured into the tube, and the time taken for the fluid to be absorbed into the core of the diaper was measured and recorded as acquisition time. After pre-determined time waiting period (20 min), a number of blotter papers (about 12) were placed on the insult area for a set of time (2.0 min) and a load (0.5 psi, 2.5 kg) was placed on top of the blotter papers. The liquid taken by the blotter papers was measured and recorded as the rewet value. The process was repeated three times to provide a picture of the multiple insult acquisition time and rewet numbers.

Acquisition and Rewet testing was conducted on a major brand diaper samples. In this test, three samples were prepared. The first sample, D1, contained a Pampers Cruisers® baby diaper (size 4). The Pampers® diaper sample had an acquisition layer between the topsheet and the absorbent core. The Pampers® acquisition layer was made of STCC fiber, and had a basis weight of 260 gsm. Sample D2 was a Pampers Cruisers® baby diaper (size 4), but the acquisition layer was removed, and a sample of LDM 2 was placed underneath the core (between the core and the backsheet). Sample D3 was a Pampers Cruisers® baby diaper (size 4), but the acquisition layer was removed and replaced with LDM 2 (dimensions=2.3 cm×7.5 cm; basis weight=160 gsm; and density=0.1 g/cc).

Figure 4:
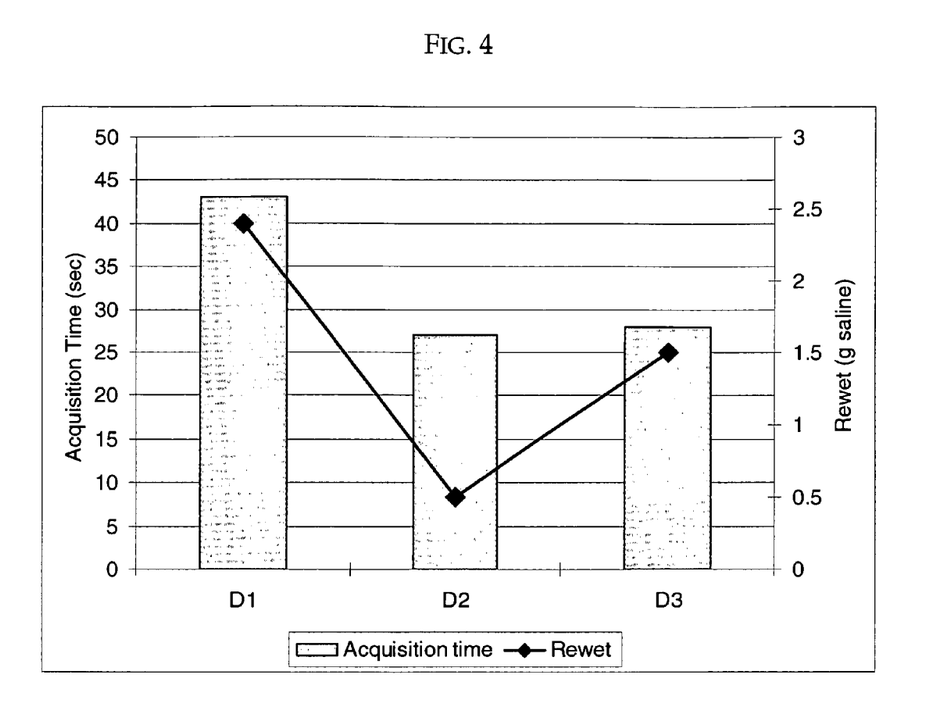
FIG. 4 is a graph showing Acquisition and Rewet of a liquid distribution layer (LDM 2, see Table 2 for specifications) placed in a Pampers Cruisers® Brand Size 4 diaper sample, as described in Example 4, as compared to Acquisition and Rewet performance for Pampers Cruisers® Brand Size 4 diaper, as commercially available.

The results of the acquisition and rewet testing are shown in FIG. 4. FIG. 4 shows that the liquid distribution mat made from enhanced fiber significantly enhanced the performance of Pampers® diaper. The Pampers® samples with a liquid distribution mat placed either over or below the absorbent core exhibited lower acquisition times and rewet values than Pampers® with STCC acquisition fiber. The results indicate that disposing a liquid distribution mat in an absorbent article provided better distribution and more complete utilization of the absorbent article.

While the invention has been described with reference to particularly preferred embodiments and examples, those skilled in the art recognize that various modifications may be made to the embodiments without departing from the spirit and scope thereof.

What is claimed is:

1. A liquid distribution mat comprising a wet-laid mat of enhanced cellulosic fibers, wherein the enhanced cellulosic fibers are cellulosic fibers cross-linked in sheet form and have:
   less than 4.5 weight % cross-linking agent;
   a kink angle of less than about 50° and less than 2 kinks per millimeter;
   wherein the wet-laid mat has:
   a basis weight of from about 100 to about 400 grams per square meter;
   a density of from about 0.05 to about 0.15 grams per cubic centimeter;
   a Free Volume of from about 5 mL/g to about 12 mL/g;
   a Vertical Absorption Height of greater than about 10 centimeters; and
   a Vertical Desorption Height that is not more than 200% of the Vertical Absorption Height.

2. The liquid distribution mat of claim 1, wherein the cellulosic fibers comprise conventional cellulosic fibers derived from hardwood cellulose pulp, softwood cellulose pulp, or combinations or mixtures thereof.

3. The liquid distribution mat of claim 1, wherein the cellulosic fibers comprise hardwood cellulose pulp selected from the group consisting of: gum, maple, oak, eucalyptus, poplar, beech, aspen, and combinations and mixtures thereof.

4. The liquid distribution mat of claim 1, wherein the cellulosic fibers comprise softwood cellulose pulp selected from the group consisting of: Southern pine, White pine, Caribbean pine, Western hemlock, spruce, Douglas fir, and mixtures and combinations thereof.

5. The liquid distribution mat of claim 1, wherein the cellulosic fibers are caustic-treated cellulosic fiber.

6. The liquid distribution mat of claim 1, wherein the cellulosic fibers are non-bleached, partially bleached, or fully bleached cellulosic fibers.

7. The liquid distribution mat of claim 1, wherein the enhanced cellulosic fiber has a centrifuge retention capacity of less than about 0.7 grams of saline per gram of oven dried fiber, and has an absorbent capacity of greater than about 12.0 grams of saline per gram of oven dried fibers.

8. The liquid distribution mat of claim 1, having a wet tensile to dry tensile ratio of about 0.7 to about 0.9, and a tensile index of about 0.3 Nm/g about 1.0 Nm/g.

9. The liquid distribution mat of claim 1, having a basis weight of about 120 gsm to about 360 gsm, a density of about 0.08 g/cc to about 0.13 g/cc, and a tensile index of about 0.8 Nm/g.

10. The liquid distribution mat of claim 1, having a Vertical Wicking Height of 20 centimeters in less than about 3.0 minutes.

11. The liquid distribution mat of claim 1, having a Vertical Wicking Height of 15 centimeters in less than about 2.5 minutes.

12. The liquid distribution mat of claim 1, wherein the liquid distribution mat vertically wicks 7.0 g of saline to a height of 5 cm in not more than about 10 seconds.

13. The liquid distribution mat of claim 1, wherein the liquid distribution mat vertically wicks at least about 20.0 g of saline to a height of 20 cm in not more than 230 seconds.

14. The liquid distribution mat of claim 1, wherein the liquid distribution mat vertically wicks at least about 25.0 g of saline to a height of 20 cm in about 3 minutes to about 8 minutes.

15. The liquid distribution mat of claim 1, having a Vertical Wicking Absorbent Capacity of at least about 6.0 grams saline/gram liquid distribution mat (g/g) at a vertical height of about 4 inches.

16. The liquid distribution mat of claim 1, having a Vertical Wicking Absorbent Capacity of at least about 4.0 g/g at a vertical height of about 8 inches.

17. The liquid distribution mat of claim 1, having a Vertical Wicking Absorbent Capacity of at least about 2.0 g/g at a vertical height of about 12 inches.

18. The liquid distribution mat of claim 1, having a Vertical Absorption Height of more than about 12 centimeters.

19. An absorbent article comprising the liquid distribution mat of claim 1.

20. The absorbent article of claim 19, wherein the absorbent core has a top sheet, a back sheet, and a storage layer disposed at least partially between the top sheet and backsheet.

21. The absorbent article of claim 20, wherein the liquid distribution mat is disposed at least partially between the top sheet and the storage layer.

22. The absorbent article of claim 20, wherein the liquid distribution mat is disposed at least partially between the back sheet and the storage layer.

23. The absorbent article of claim 19, wherein the absorbent article is selected from the group consisting of a diaper, an incontinent device, a feminine hygiene product, a wipe, a bandage, a bed pad, and any combination thereof.

24. The absorbent article of claim 20, wherein the liquid distribution mat has an area that is about 30% to about 100% of the area of the storage layer.

25. The liquid distribution mat of claim 1, wherein the liquid distribution mat comprises a bi-component synthetic fiber selected from the group consisting of polypropylene, polyethylene, bi-component fibers, and combinations thereof.

26. The liquid distribution mat of claim 25, wherein the liquid distribution mat comprises from about 1% to about 10% of the bi-component synthetic fiber.

27. The liquid distribution mat of claim 25, wherein the liquid distribution mat comprises up to about 3% of the bi-component synthetic fiber.

28. The liquid distribution mat of claim 25, wherein the bi-component fiber has a core comprising polyethylene and polyester.

29. The liquid distribution mat of claim 1, wherein the liquid distribution mat further compromises a wet strength agent.

30. The liquid distribution mat of claim 29, wherein the wet strength agent is retained in the fibers after wet-laying and pressing from about 0.2 weight % to about 5 weight %, based on the weight of the wet-laid structure.

31. The liquid distribution mat of claim 29, wherein the wet strength agent is added to the fiber during the wet-laying process.

32. The liquid distribution mat of claim 29, wherein the wet strength agent is selected from the group consisting of Kymene 557H, PAREZ 631 NC, chloroxylated polyacrylamides, HERCOBOND 1366, and glyoxylated polyacrylamide.

* * * * *